United States Patent [19]

Graham et al.

[11] 4,207,262

[45] Jun. 10, 1980

[54] CHEMICAL PROCESS FOR REDUCING THE CYCLOHEXANONE CONTENT OF CRUDE ANILINE

[75] Inventors: Alan J. Graham; Arthur Ibbotson, both of Manchester, England

[73] Assignee: Imperial Chemical Industries Limited, London, England

[21] Appl. No.: 41,256

[22] Filed: May 21, 1979

[30] Foreign Application Priority Data

Jun. 8, 1978 [GB] United Kingdom ............... 26546/78

[51] Int. Cl.$^2$ ............................................. C07C 85/26
[52] U.S. Cl. ................................... 260/582; 260/701
[58] Field of Search ............... 260/582, 580, 578, 701

[56] References Cited

U.S. PATENT DOCUMENTS 2,408,975 10/1946 Engel ............................... 260/582 X
3,442,938 5/1969 Christensen et al. ............ 260/582 X

FOREIGN PATENT DOCUMENTS 49-35341 4/1974 Japan ........................................ 260/578
982903 2/1965 United Kingdom ..................... 260/580

OTHER PUBLICATIONS

Emel' Yanov et al., "Vestsi Akad, Navuk Belarus, SSR, Ser. Khim. Navuk", vol. 3, pp. 88–91 (1972).

Primary Examiner—John Doll
Attorney, Agent, or Firm—Cushman, Darby & Cushman

[57] ABSTRACT

A process for reducing the cyclohexanone content of crude aniline that has been prepared by the catalytic hydrogenation of nitrobenzene comprising treating the crude aniline with phosphoric acid or an alkyl or chloroalkyl ester thereof.

2 Claims, No Drawings

CHEMICAL PROCESS FOR REDUCING THE CYCLOHEXANONE CONTENT OF CRUDE ANILINE

This invention relates to a chemical process and more particularly to a process for reducing the level of impurities present in crude aniline that has been prepared by the conventional hydrogenation of nitrobenzene.

The manufacture of aniline by the catalytic hydrogenation of nitrobenzene is an established industrial process. The conversion of nitrobenzene to aniline takes place in very high yields but, in addition to the main reaction, some unwanted side reactions take place resulting in the formation of impurities. One of these impurities is cyclohexanone which is difficult to remove from the aniline by normal physical methods such as distillation.

It has now been found that the cyclohexanone content of the aniline can be reduced by a chemical treatment as hereinafter described.

Thus, according to the invention, there is provided a process for reducing the cyclohexanone content of crude aniline that has been prepared by the catalytic hydrogenation of nitrobenzene comprising treating the crude aniline with phosphoric acid or an alkyl or chloroalkyl ester thereof.

The crude aniline treated according to the invention may have been prepared by any batch or continuous process involving the catalytic hydrogenation of nitrobenzene. Catalysts involved in the hydrogenation include Raney nickel, palladium on charcoal or supported nickel, cobalt or copper and especially nickel-on-kieselguhr.

One continuous process for the manufacture of aniline by the liquid phase catalysed hydrogenation of nitrobenzene is described in our United Kingdom Pat. No. 982,903 and is characterised in that the concentration of aniline in the liquid phase is not less than 95% by weight and in that the hydrogenation is conducted at the apparent boiling point of the reaction mixture at a pressure not exceeding 10 atmospheres, at least some of the heat of the reaction being removed by allowing the reaction mixture to evaporate, the vapours being condensed, water separated from the condensate and when necessary sufficient of the condensed aniline being returned to the reactor to maintain steady conditions therein.

The product of the hydrogenation process is crude aniline usually containing some water and small amounts of cyclohexanone and other impurities. In accordance with the invention, this crude aniline is treated with phosphoric acid or an alkyl,chloroalkyl or acid alkyl ester thereof at ambient or elevated temperatures. It is believed that during the treatment the cyclohexanone reacts with aniline to form cyclohexylidene aniline. The water which is also formed in this reaction can be removed by azeotropic distillation and accordingly it is convenient to carry out the treatment at the boiling point of the crude aniline using normal or reduced pressures.

The amount of phosphoric acid or ester thereof used in the treatment can be varied over a wide range, for example 10 ppm to 5%. An amount of about 50 ppm on the weight of crude aniline is suitable. The preferred agent is phosphoric acid. It may be employed as an aqueous solution of any convenient strength, for example 10% aqueous, up to the highest strength polyphosphoric acid available.

At the end of the treatment the purified aniline may be isolated by a conventional distillation procedure.

The treatment can be carried out in completely conventional equipment, and may be operated as a batch or continuous process.

The invention is illustrated but not limited by the following Examples 8,13–16, 18,19 and 21 in which all parts and percentages are by weight. The remaining Examples are included for comparison.

EXAMPLE 1

Aniline containing 1% of cyclohexanone as impurity was heated at 130° C. for 90 minutes and the increase in water content of the mixture found and compared with the maximum increase theoretically possible according to the equation

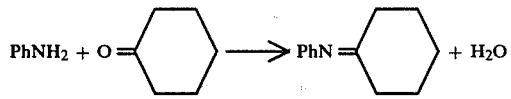

In absence of catalyst the water content change indicated 27% of the maximum possible amount to have been formed.

EXAMPLES 2–10

This experiment was repeated in the presence of 50 ppm of a number of possible catalysts with the results shown.

| Example | Agent | Water formed : % of theoretical maximum amount |
|---|---|---|
| 2 | Boric acid | 40.5 |
| 3 | 2-Ethylhexoic acid | 67.6 |
| 4 | Formic acid | 27.0 |
| 5 | Citric acid | 67.6 |
| 6 | Benzenesulphonic acid | 54.1 |
| 7 | Sulphuric acid | 33.8 |
| 8 | 85% Phosphoric acid | 94.6 |
| 9 | Methane sulphonic acid | 60.8 |
| 10 | Potassium hydroxide | 40.5 |

These results clearly demonstrate the effectiveness of phosphoric acid in promoting the removal of cyclohexanone by reaction with aniline.

EXAMPLES 11–16

Aniline containing 1,000 ppm of cyclohexanone as impurity was heated at 132° C. in the presence of 50 ppm of a catalyst and samples analysed at intervals for cyclohexanone by GLC.

| Example | Agent | Time to 50 ppm cyclohexanone |
|---|---|---|
| 11 | None | >90 minutes |
| 12 | Triphenylphosphoramide | 65 |
| 13 | Triethyl phosphate | 20 |
| 14 | 85% Phosphoric acid | 30 |
| 15 | Tris-(chloropropyl) phosphate | 30 |
| 16 | Tris-(chloroethyl) phosphate | 20 |

EXAMPLES 17-19

Aniline containing 1,000 ppm of cyclohexanone as impurity was heated at 110° C. and 81 mm Hg pressure so that the aniline distilling from the flask was condensed and any water present removed before return of aniline to the reactor using a Dean and Stark separator. Cyclohexanone content was determined by GLC at intervals.

| Example | Agent (50 ppm)       | Time to 50 ppm cyclohexanone |
|---------|----------------------|------------------------------|
| 17      | None                 | 70 minutes                   |
| 18      | Triethyl phosphate   | 42                           |
| 19      | 85% Phosphoric acid  | 30                           |

EXAMPLES 20-21

Similar experiments at 180° C./760 mm also under azeotropic drying conditions gave similar results.

| Example | Agent                | Time to 50 ppm cyclohexanone |
|---------|----------------------|------------------------------|
| 20      | None                 | 20 minutes                   |
| 21      | 85% phosphoric acid  | 8                            |

We claim:
1. A process for reducing the cyclohexanone content of crude aniline that has been prepared by the catalytic hydrogenation of nitrobenzene comprising treating the crude aniline with from 10 ppm to 5%, based on the weight of crude aniline, of phosphoric acid or lower alkyl or chloro lower alkyl ester thereof.
2. A process as claimed in claim 1 wherein the phosphoric acid or ester thereof is used in an amount of about 50 ppm on the weight of crude aniline.

* * * * *